United States Patent
Lanzoni

Patent Number: 5,715,604
Date of Patent: Feb. 10, 1998

[54] FORCE-DEVELOPING DEVICE FOR CUTTING FORCEPS

[75] Inventor: Maurice Lanzoni, Chaumont, France

[73] Assignee: EIS Instruments, Chaumont, France

[21] Appl. No.: 663,717

[22] Filed: Jun. 14, 1996

[30] Foreign Application Priority Data

Jun. 15, 1995 [FR] France .................. 95 07157

[51] Int. Cl.$^6$ .................................................. B26B 17/02
[52] U.S. Cl. ........................... 30/192; 30/187; 30/245; 30/252
[58] Field of Search .................. 30/175, 186, 187, 30/188, 189, 190, 191, 192, 193, 194, 244, 245, 250, 251, 252, 183, 184, 185

[56] References Cited

U.S. PATENT DOCUMENTS

| 416,500 | 12/1889 | Robbins | 30/190 |
|---|---|---|---|
| 1,741,971 | 12/1929 | Bodendieck | 30/252 |
| 2,341,654 | 2/1944 | Richter | 30/192 |
| 3,039,189 | 6/1962 | McBerty | 30/245 |
| 3,273,240 | 9/1966 | Florian | 30/192 |
| 3,893,237 | 7/1975 | Jahnke | 30/187 |
| 4,254,549 | 3/1981 | McMullin | |
| 4,644,651 | 2/1987 | Jacobsen | 30/251 |
| 5,046,250 | 9/1991 | Huang | |

FOREIGN PATENT DOCUMENTS

| 0 542 437 | 5/1993 | European Pat. Off. |
| 1162295 | 9/1958 | France |
| 41 31 494 | 4/1993 | Germany |
| WO94/00059 | 1/1994 | WIPO |

*Primary Examiner*—Hwei-Siu Payer
*Attorney, Agent, or Firm*—Young & Thompson

[57] ABSTRACT

A force-developing device for forceps of the type equipped with two jaw elements (2, 3) and with two handles (4, 5) includes a jaw (6A). A link rods system (6B) is articulated with the jaw (6A). A front end of a piston (7) is connected to the link rods system (6B). The piston is housed slidingly inside a first handle (4). A yoke (8) is provided for holding the second handle (5) relative to the first handle (4). A pair of complementary racks (9) mechanically drive the piston (7), the pair being borne by each of the two handles (4, 5). A trigger catch and a rack for preventing the return of the piston are borne by the first handle (4). The pair of complementary racks (9) for driving the piston (7), the trigger catch, and the rack acts alternately on the piston so that by successively moving the second handle (5) towards and away from the first handle (4), the piston (7) is moved forwards and the jaw (6A) is deformed by means of the link rods system (6B). The successive movement brings the two jaw elements (2, 3) towards each other.

14 Claims, 5 Drawing Sheets

FORCE-DEVELOPING DEVICE FOR CUTTING FORCEPS

BACKGROUND OF THE INVENTION

1. Field of the Invention

The present invention relates to a force developing device for forceps of the type equipped with two jaw elements and with two handles. It applies in particular surgical cutting forceps.

2. Description of the Prior Art

In surgical operations, for example spinal osteosynthesis or elastic central medullary nailings, it is common for metal rods or plates to be employed to produce osteosynthesis assemblies or for fixating fragments of bone resulting from a fracture.

In the case of interventions on the spine using rods or plates, various situations may arise.

During the preparation of adapting the plates or rods to the dimensions of the anatomy of the patient, the surgeon has to be able to cut these plates or rods to the correct length, holding the implant in one hand and cutting the plates or rods with the other hand using forceps, developing minimum force.

Moreover, at the end of the intervention, when the reductions have been made and the fixations have been achieved, some parts at the ends of the osteosynthesis assemblies become protruding and therefore undesirable. These ends also have to be taken away by lopping off in situ.

In the case of the removal of these osteosynthesis assemblies which have become undesirable after consolidation, it is sometimes the case that the rods or plates cannot be withdrawn simply by opening the fixations connecting these rods together. It is therefore indispensible to lop off the rods or the plates on each side of the hooks and of the pedicle screws in order to be able to extract them without being hampered by the long rods.

In various cases, it is also necessary to be able to work within the space allowed by the anatomy, which is very small. It is therefore necessary to be able to supply the energy needed to cut through the implants.

In the case of the fitting or removal of metal rods or of central medullary nails, the access incisions are reduced the absolute minimum necessary in order to promote rapid and discrete subsequent scarring.

In such small and shallow openings it is necessary either to go and cut off the excesses at the ends of the rods, or go and grip the remaining end in the case of removal by extraction.

Furthermore, in the case of lopping off, the jaw elements of the forceps must have small bulk and be able to withstand the cutting force.

In the case of the extraction of the rods, the purchase on the available part of the rod has to be achieved by extremely powerful clamping so that it does not slip under the force of extraction.

In general, the jaw elements and the forceps used for this work have to develop a substantial clamping power, whilst being of very small bulk to allow interventions in situ in spaces allowed by the anatomy, which are very small.

Now, the forceps normally employed have a limited cutting capability and do not allow rods of a diameter substantially of the region of 7 mm to be cut. In the contrary case, the bulk of their jaw elements is such that any work in situ is prohibited, and what is more the handling of such forceps is laborious and may even become dangerous. Indeed, the forces required to chop through rods demand the simultaneous action of two individuals on these forceps, the length of whose lever arms exceed 0.5 m. This may cause the surgeon to lose control over the operation act he is performing.

Moreover, the known forceps are specially designed for a specific surgical need: they cannot be both cutting forceps and clamping forceps.

SUMMARY OF THE INVENTION

The object of the invention is to provide surgical forceps which overcome the aforementioned drawbacks, that is to say which are modular and of small bulk while developing substantial power and which can be manipulated with just one hand and for this to be achieved using simple, effective and inexpensive means.

To this end the subject of the invention is a force developing device for forceps of the type equipped with two jaw elements and with two handles, characterized in that it includes:

- a jaw formed of two link rods cranked in opposite directions and articulated, at their cranked part, independently of one another, the two jaw elements being positioned at one of their ends;
- a link rods system articulated with the two link rods of the jaw, the jaw and link rods system assembly having substantially the shape or a deformable quadrilateral;
- a piston connected by its front end to the link rods system at one vertex of this system opposite the vertex of the jaw bearing the jaw elements, the piston being housed inside a first handle and guided in slidingly thereby;
- means for holding the second handle relative to the first handle, these being integral with the piston and bearing against the first handle;
- complementary means rot mechanically driving the piston inside the first handle, these means being borne by each of the two handles; and
- means for preventing the return of the piston, these means being borne by the first handles;
- the complementary means for driving the piston and the non-return means acting alternately on this piston so that by successively moving the second handle towards and away from the first handle the piston is moved forwards and the jaw is deformed by means of the link rods system, so that the two jaw elements are brought towards each other.

The developing device according to the invention may include one or more of the following features:

- the mechanical drive means comprise a first rack borne fixedly by the first handle and a second rack with a shorter length than the first rack, articulated to the second handle and placed facing the first rack so that they mesh with one another when the two handles are brought close together;
- the mechanical drive means comprise a rack borne fixedly by the first handle and a pawl borne by the second handle so as to interact with the said rack when the two handles are brought closer together;
- the device includes elastic means borne by the two handles so as to urge these handles apart and to apply the second rack or the pawl to the first rack when the handles are brought closer together;
- the link rods system comprises two pairs of link rods, each pair being articulated to the front end of the piston and to one of the two link rods of the jaw;

the means for preventing the return of the piston comprise a trigger catch borne by the first handle and interacting with an additional rack placed on the piston;

the means for holding the second handle relative to the first handle comprise a yoke oriented away from the first rack, and the two cheeks of which are parallel and situated on each side of the first handle;

the rear ends of the cheeks are integral with the piston and the second handle is articulated by two pivots placed at the front of the cheeks;

the yoke bears against the first handle by means of a roller on the opposite face of the first handle from the one bearing the first rack;

the means for preventing the return of the piston can be disengaged;

the device includes elastic means urging the piston backwards when the non-return means are disengaged; and the jaw elements are removable jaw elements.

A further subject of the invention is cutting forceps comprising the device defined as hereinabove, and in which the jaw elements are either shears elements, or clamping elements.

BRIEF DESCRIPTION OF THE DRAWINGS

One embodiment will now be described with reference to the attached drawings, in which.

DESCRIPTION OF THE PREFERRED EMBODIMENTS

Figure 1:
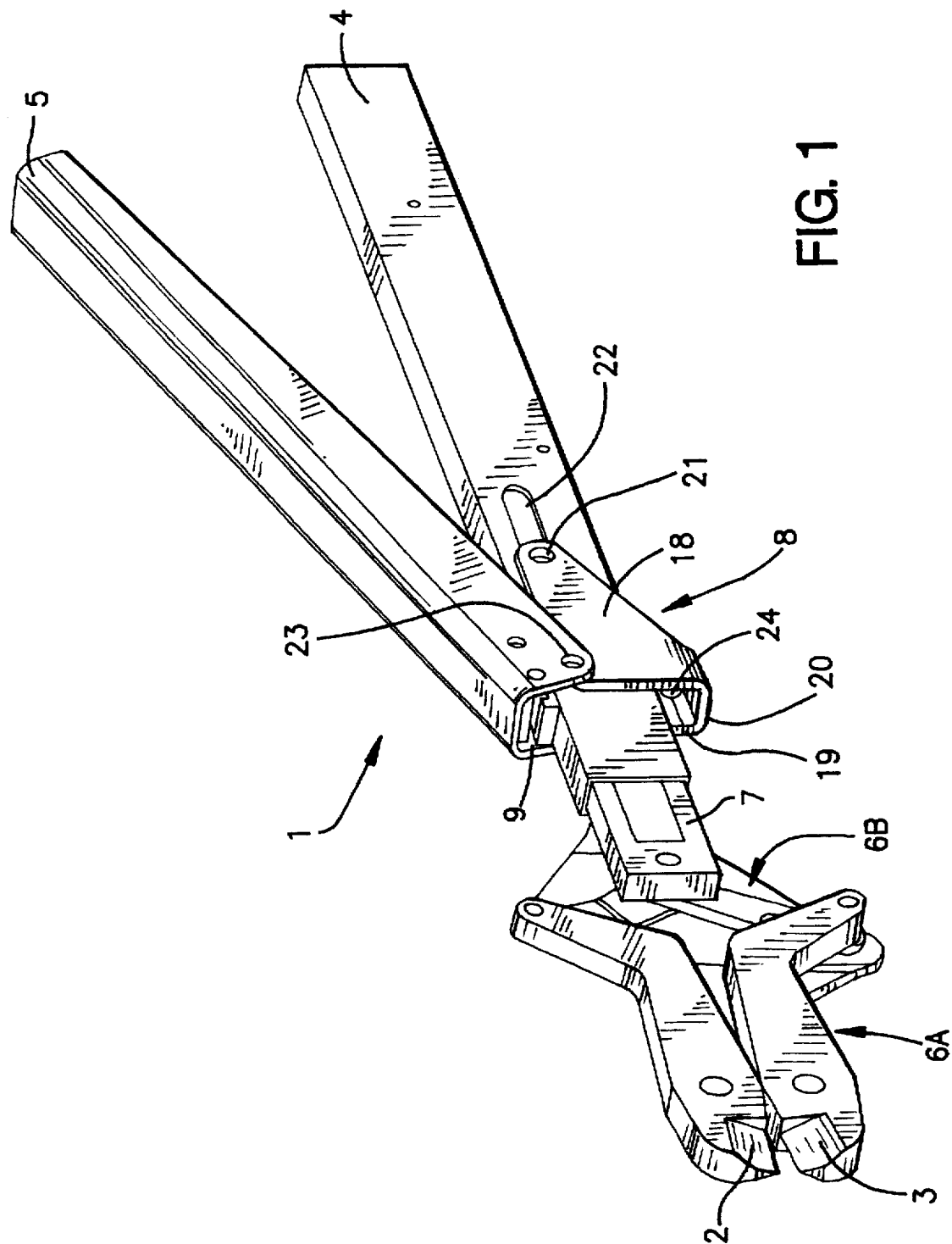
FIG. 1 is a perspective view of forceps and of their force-developing device according to the invention.
Figure 2:
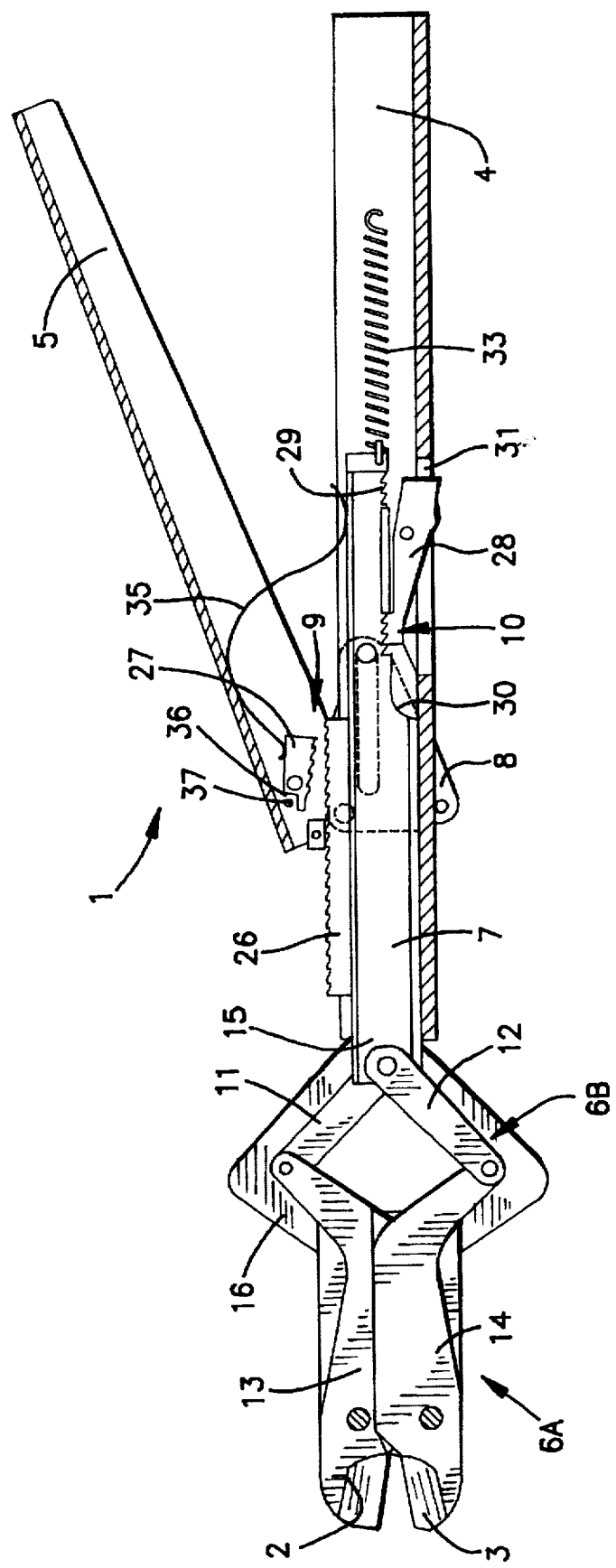
FIG. 2 is a longitudinal section of the force-developing device of FIG. 1, in the position rest.

The force-developing device 1 represented in FIGS. 1 and 2 is applied to forceps equipped with two jaw elements 2 and 3 and with two handles, a first handle 4 or stationary handle and a second handle 5, or mobile handle. The mobile handle 5 has a U-shaped cross-section and the stationary handle 4 is hollow and of rectangular cross-section, the handle 5 being shorter than the handle 4. These two handles 4 and 5 can be made either of plastic or of metal.

The force-developing device 1 includes a jaw 6A and a link rods system 6B connected to a piston 7 housed in the stationary handle 4, means 8 for holding the mobile handle 5 relative to the stationary handle 4, complementary means 9 for mechanically driving the piston 7 inside the stationary handle 4 and means 10 for preventing the return of the piston 7.

The link rods system 6B is articulated to the jaw 6A. It consists of two pairs of link rods 11 and 12 (for the clarity of the drawings, just one link rod in two has been represented for each pair). Each pair of link rods 11 and 12 includes two straight parallel link rods. The jaw 6A has two link rods 13 and 14 which are cranked, at their front end, in opposite directions. The set of four link rods 11 to 14 is arranged so that it substantially forms a quadrilateral.

The rear ends of the pairs of link rods 11 and 12 are each articulated to the front end 15 of the piston 7 and on each side thereof, while the front ends of these link rods are respectively articulated with the rear ends of the link rods 13 and 14. The front ends of these link rods 13 and 14 are independently articulated at two separate points placed on a flange 16 fixed to the stationary handle 4. The front ends of these last two link rods respectively bear the jaw elements 2 and 3.

The piston 7, which has a rectangular cross-section, is slidingly housed in the stationary handle 4.

The means 8 for holding the mobile handle 5 relative to the stationary handle 4 include a yoke 8 slipped over the stationary handle 4. This yoke 8 includes two cheeks 18 and 19 of triangular shape which are connected by a flat rim part 20. The rear ends of the cheeks 18 and 19 are integral with the piston 7 via tenons 21. These tenons 21 slide inside two longitudinal slots 22 formed in each of the lateral faces of the stationary handle 4. The front end of the mobile handle 5 is articulated to the yoke 8 by means of two pivots 23 placed on the front ends of the cheeks 18 and 19.

The yoke 8 bears against the face of the stationary handle 4 situated away from the mobile handle 5. This bearing is a sliding bearing achieved by means of a roller 24.

The complementary means 9 for mechanically driving the piston 7 inside the stationary handle 4 include a first rack 26 borne fixedly by that face of the stationary handle 4 which is situated facing the mobile handle 5, and a second rack 27 borne so that it can be rotated by the interior face of the mobile handle 5. The second, rotary, rack 27 is markedly shorter than the first, stationary, rack 26 and is placed facing it.

As an alternative, the second rack 27 may be replaced by a pawl also borne internally by the handle 5 and able to rotate or using any other suitable device.

The means 10 for preventing the return of the piston 7 consist of a trigger catch 28 and of a rack 29. The rear end of the trigger catch 28 is borne so that it can be rotated by the interior face of the stationary handle 4 so that this trigger catch is situated facing a recess 30 formed in the rear part of the piston 7. The front end of this trigger catch 28 carries toothing which faces the rack 29 borne by the recess 30 and the rear end extends out of the handle 4 through an opening 31.

The rear end of the piston 7 is furthermore connected to the front end of a spring 33, the rear end of which is home by the interior face of the rear end of the stationary handle 4.

Elastic means of the leaf spring type 35 are interposed between the stationary handle 4 and the mobile handle 5. This leaf spring has an S shape overall, the rear end of which is fixed to the face of the stationary handle 4 facing the mobile handle 5 and the front end of which bears against the opposite face of the rack 27 from the toothing of this rack, a crest of this leaf spring 35 bearing against the interior face of the mobile handle 5.

The front end of the rotary rack 27 has a projection 36 intended to come into abutment, under the action of the leaf spring 35, against a stub 37 placed in one of the lateral faces of the mobile handle 5.

Although this is not represented in the figures, the jaw elements 2 and 3 may be removable elements, of the shears element or clamping element type.

The operation of this device will now be explained with reference to FIGS. 2 to 5.

At rest, that is to say when no action is exerted on these forceps, the two handles, stationary 4 and mobile 5, are urged apart by the leaf spring 35. The piston 7 is urged backwards by the spring 33, the trigger catch 28 of the rack 29 having previously been disengaged. The jaw elements 2 and 3 are thus apart. Likewise, the racks 26 and 27 do not mesh with one another and the rear end of the rack 26 is placed facing the rack 27.

Figure 3:
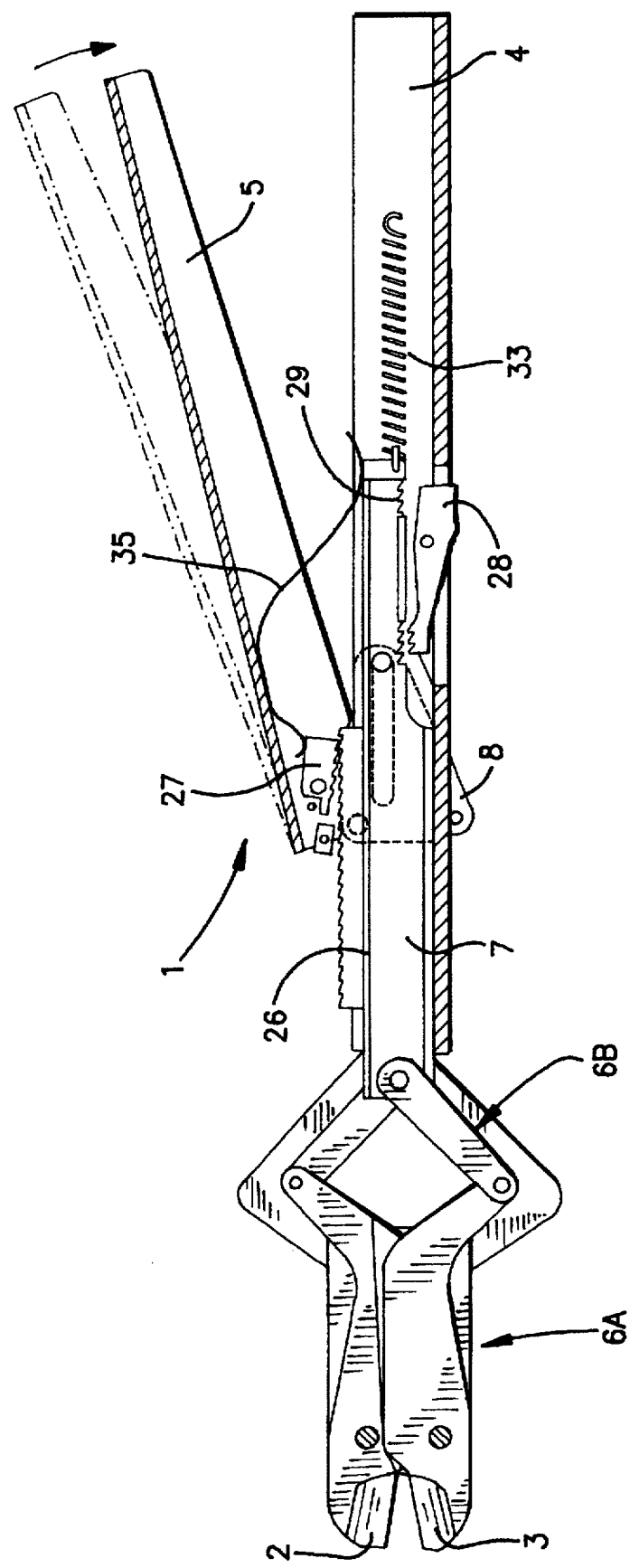
FIGS. 3 to 5 are longitudinal sections through the force-developing device of FIG. 1, represented in the successive states leading to closure of the jaw elements of the forceps.
Figure 4:
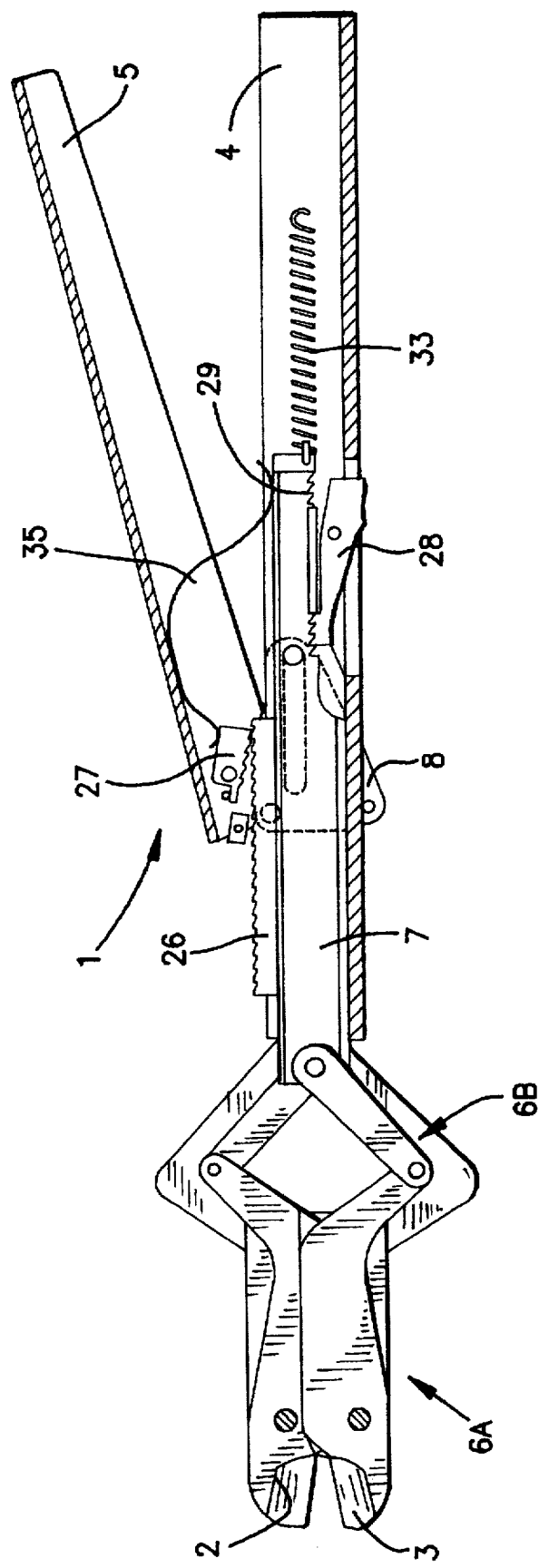
Figure 5:
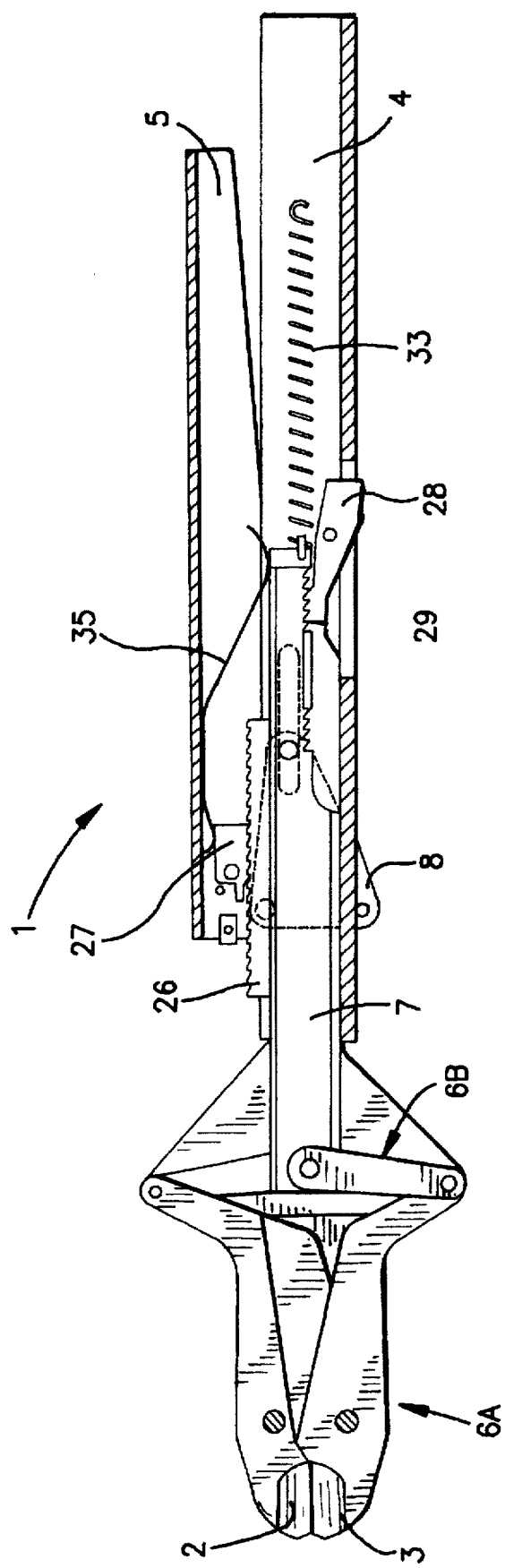

When a cutting or clamping action is to be exerted using the jaw elements 2 and 3, an action is exerted on the mobile handle 5 so as to bring the two handles 4 and 5 closer together (FIG. 3). The racks 26 and 27 therefore mesh with one another, which causes the piston 7 to move forward inside the stationary handle 4. This forward movement continues until all the teeth of the rack 27 are meshing with the teeth of the rack 26 and causes a forwards deformation of the link rods system 6B together with a separation of the rear ends of the two link rods 13, 14 of the jaw 6A by rotation. This separation of the two link rods 13 and 14 leads the jaw elements 2 and 3 to move towards each other for the first time. The toothing on the trigger catch 28 therefore interacts with the toothing 29 placed at the rear of the piston 7, which locks this piston in position.

The force on the mobile handle 5 can then be released, which frees the rack 27 from the rack 26, keeping the jaw elements 2 and 3 together.

With an action identical to the previous one, the two handles. Stationary 4 and mobile 5, are brought together again, and the piston 7 is then driven forwards again. This forward movement closes the jaw elements 2 and 3 a little more. By successively moving the mobile handle 5 towards and away from the stationary handle 4, that is to say with a movement similar to a pumping movement, the jaw elements 2 and 3 are progressively brought closer together until firm clamping or a very high cutting force is obtained (FIG. 5), and this is achieved in eight or nine successive pumping actions.

When the jaw elements 2 and 3 are to be moved apart again, all that is required is for the toothing of the trigger catch 28 to be released from the toothing of the rack 29 of the piston 7 by pressing on the rear end of this trigger catch 28. The spring 33 then returns the piston 7 backwards.

This force-developing device for forceps has the advantage of developing very high clamping or cutting forces with the exertion of a simple pumping action on the handles of these forceps, using just one hand. This device is therefore of very small bulk, allowing easy intervention in situ. What is more, since the force required for complete cutting is obtained in several pumping actions, the jaw elements are subjected to considerably reduced stress by comparison with the case in which the force is applied in a single maneuver, so that the sections of the said jaw elements can be reduced correspondingly, which contributes to their small bulk.

What is claimed is:

1. A hand-held device comprising:

two jaw elements a first handle and a second handle;

a jaw formed of two link rods cranked in opposite directions and articulated, at their cranked part, independently of one another, each of the two jaw elements being at an end of a respective one of said two link rods;

a link rods system articulated with the two link rods of the jaw, the jaw and the link rods system having substantially a shape of a deformable quadrilateral;

a piston connected by its front end to the link rods system at one vertex of the link rods system opposite the vertex of the jaw, the piston being slidingly housed inside the first handle;

means for holding the second handle relative to the first handle, said means for holding being integral with the piston and bearing against the first handle;

complementary means for mechanically driving the piston inside the first handle, said complementary means being borne by each of the two handles; and means for preventing the return of the piston, said means for preventing being borne by the first handle;

the complementary means and the means for preventing acting alternately on the piston so that by successively moving the second handle towards and away from the first handle the piston is moved forwards and the jaw is deformed by means of the link rods system, so that the two jaw elements are brought towards each other.

2. The device according to claim 1, wherein the complementary means comprise a first rack borne fixedly by the first handle and a second rack with a shorter length than the first rack articulated to the second handle and placed facing the first rack so that said first and second racks mesh with one another when the two handles are brought closer together.

3. The device according to claim 2, further comprising elastic means borne by the two handles so as to urge these handles apart and to apply a pawl to the first rack when the handles are brought closer together.

4. The device according to claim 1, wherein the complementary means comprise a rack borne fixedly by the first handle and a pawl borne by the second handle so as to interact with said rack when the two handles are brought closer together.

5. The device according to claim 1, wherein the link rods system comprises a further two pairs of link rods, each said pair being articulated to the front end of the piston and to one of the two link rods of the jaw.

6. The device according to claim 1, wherein the means for preventing the return of the piston comprise a trigger catch borne by the first handle and interacting with a rack placed on the piston.

7. The device according to claim 1, wherein the means for holding the second handle relative to the first handle comprise a yoke oriented away from a first rack, said yoke having two parallel cheeks situated on each side of the first handle.

8. The device according to claim 7, wherein rear ends of the cheeks are integral with the piston and the second handle is articulated by two pivots placed at the front of the cheeks.

9. The device according to claim 7, wherein the yoke bears against the first handle by means of a roller on an opposite face of said first handle from a face bearing the first rack.

10. The device according to claim 1, wherein the means for preventing the return of the piston can be disengaged.

11. The device according to claim 10, further comprising elastic means urging the piston backwards when the preventing means are disengaged.

12. The device according to claim 1, wherein the jaw elements are removable jaw elements.

13. The device according to claim 1, wherein the jaw elements are shears elements.

14. The device according to claim 1, wherein the jaw elements are clamping elements.

* * * * *